(12) United States Patent
Li et al.

(10) Patent No.: US 12,376,195 B2
(45) Date of Patent: Jul. 29, 2025

(54) MODIFICATION LAYER ON SURFACE OF CERAMIC SUBSTRATE AND PREPARATION METHOD THEREFOR, CERAMIC HEATING BODY AND ELECTRONIC ATOMIZATION DEVICE

(71) Applicant: SHENZHEN SMOORE TECHNOLOGY LIMITED, Guangdong (CN)

(72) Inventors: Pei Li, Shenzhen (CN); Zhenlong Jiang, Shenzhen (CN); Hongxia Lv, Shenzhen (CN); Congwen Xiao, Shenzhen (CN); Lingrong Xiao, Shenzhen (CN); Xiaoping Li, Shenzhen (CN)

(73) Assignee: SHENZHEN SMOORE TECHNOLOGY LIMITED, Shenzhen (CN)

( * ) Notice: Subject to any disclaimer, the term of this patent is extended or adjusted under 35 U.S.C. 154(b) by 744 days.

(21) Appl. No.: 17/746,633

(22) Filed: May 17, 2022

(65) Prior Publication Data

US 2022/0279625 A1     Sep. 1, 2022

Related U.S. Application Data

(63) Continuation of application No. PCT/CN2020/120400, filed on Oct. 12, 2020.

(30) Foreign Application Priority Data

Nov. 18, 2019   (CN) .......................... 201911126520.6

(51) Int. Cl.
*H05B 3/12*     (2006.01)
*C04B 41/50*    (2006.01)
(Continued)

(52) U.S. Cl.
CPC .......... *H05B 3/12* (2013.01); *C04B 41/5024* (2013.01); *C04B 41/5035* (2013.01);
(Continued)

(58) Field of Classification Search
CPC ...... H05B 3/12; H05B 2203/017; H05B 3/02; C04B 41/5024; C04B 41/5035; C04B 41/87; C04B 2235/3472; C04B 2235/9607
(Continued)

(56) References Cited

U.S. PATENT DOCUMENTS

| | | |
|---|---|---|
| 2004/0112503 A1 | 6/2004 | Chen et al. |
| 2009/0197076 A1 | 8/2009 | Xie et al. |

(Continued)

FOREIGN PATENT DOCUMENTS

| | | |
|---|---|---|
| CN | 101538164 A | 9/2009 |
| CN | 104774036 A | 7/2015 |

(Continued)

OTHER PUBLICATIONS

Chinese Patent Office, Rejection Decision in Chinese Patent Application No. 201911126520.6 (May 25, 2022).
(Continued)

*Primary Examiner* — Phuong T Nguyen
(74) *Attorney, Agent, or Firm* — Leydig, Voit & Mayer, Ltd.

(57) ABSTRACT

A modification layer on a surface of a ceramic substrate, includes, in parts by mass: 56 to 67.5 parts of silicon dioxide; 12 to 18 parts of aluminum oxide; and 2.8 to 5.5 parts of lithium oxide. In an embodiment, the modification layer further includes, in parts by mass: at least one of 1.8 to 2.8 parts of phosphorus pentoxide; 0.5 to 2.0 parts of calcium oxide; 0.15 to 1.5 parts of magnesium oxide; and 2.5 to 5.25 parts of barium oxide.

14 Claims, 3 Drawing Sheets

(51) Int. Cl.
  *C04B 41/87* (2006.01)
  *H05B 3/02* (2006.01)

(52) U.S. Cl.
  CPC ............... *C04B 41/87* (2013.01); *H05B 3/02* (2013.01); *C04B 2235/3472* (2013.01); *C04B 2235/9607* (2013.01); *H05B 2203/017* (2013.01)

(58) Field of Classification Search
  USPC ......................................................... 219/538
  See application file for complete search history.

(56) References Cited

U.S. PATENT DOCUMENTS

| | | | |
|---|---|---|---|
| 2019/0270183 A1 | 9/2019 | Nelson et al. | |
| 2020/0196676 A1* | 6/2020 | Zhu | A24F 40/46 |

FOREIGN PATENT DOCUMENTS

| | | |
|---|---|---|
| CN | 106579564 A | 4/2017 |
| CN | 107006896 A | 8/2017 |
| CN | 208354611 U | 1/2019 |
| CN | 208403249 U | 1/2019 |
| CN | 208440276 U | 1/2019 |
| CN | 109721344 A | 5/2019 |
| CN | 110074469 A | 8/2019 |
| CN | 110407566 A | 11/2019 |
| CN | 110922213 A | 3/2020 |
| CN | 109574660 B | 1/2022 |
| WO | 2017066261 A2 | 4/2017 |

OTHER PUBLICATIONS

Wu et al., "Physical Properties of Materials (Second Edition)," East China University of Science and Technology Press, pp. 108-109 (Dec. 2018).
Gingerrey et al., "Introduction to Ceramics," China Construction Industry Press, pp. 373-374 (Dec. 1982).
Manman Liu et al., "Influence of crystallization characteristic of LAS low thermal expansion glazes on thermal shock resistance," Functional Materials, vol. 47, No. 3, Total 5 pages (Mar. 30, 2016).
Soki Yoichi, "Glazes and Colors," China Industry Press, pp. 77-80 (Dec. 31, 1979).
European Patent Office, Search Report in European Patent Application No. 20889568.0 (Nov. 14, 2023).
Patent Cooperation Treaty, International Search Report, International Application No. PCT/CN2020/120400 (Jan. 12, 2021).
Patent Cooperation Treaty, Written Opinion of the International Searching Authority, International Application No. PCT/CN2020/120400 (Jan. 12, 2021).
Chinese Patent Office, First Office Action in Chinese Patent Application No. 201911126520.6 (Mar. 19, 2021).
Chinese Patent Office, Second Office Action in Chinese Patent Application No. 201911126520.6 (Sep. 9, 2021).
Chinese Patent Office, Third Office Action in Chinese Patent Application No. 201911126520.6 (Jan. 26, 2022).

* cited by examiner

MODIFICATION LAYER ON SURFACE OF CERAMIC SUBSTRATE AND PREPARATION METHOD THEREFOR, CERAMIC HEATING BODY AND ELECTRONIC ATOMIZATION DEVICE

CROSS-REFERENCE TO PRIOR APPLICATION

This application is a continuation of International Patent Application No. PCT/CN2020/120400, filed on Oct. 12, 2020, which claims priority to Chinese Patent Application No. CN 201911126520.6, filed on Nov. 18, 2019. The entire disclosure of both applications is hereby incorporated by reference herein.

FIELD

This application relates to the field of ceramic materials, and in particular, to a modification layer on a surface of a ceramic substrate, a preparation method of a modification layer, a ceramic heating body, and an electronic atomization device.

BACKGROUND

A ceramic heating body is one of the core components of an electronic atomization device. Compared with a conventional glass fiber cotton wire wound heating body, a novel ceramic heating body includes porous ceramics wound with a heating wire or porous ceramics printed with a resistance paste on the surface, thus achieving strong lipophilicity, uniform heating, high temperature resistance, no dry burning, and other advantages. However, a modification layer in the current ceramic heating body has poor thermal shock resistance and is prone to microcracks, which may cause a heating layer of the ceramic heating body to be easily torn off during long-term use, restricting the improvement of the service life of the ceramic heating body.

SUMMARY

In an embodiment, the present invention provides a modification layer on a surface of a ceramic substrate, comprising, in parts by mass: 56 to 67.5 parts of silicon dioxide; 12 to 18 parts of aluminum oxide; and 2.8 to 5.5 parts of lithium oxide.

BRIEF DESCRIPTION OF THE DRAWINGS

Subject matter of the present disclosure will be described in even greater detail below based on the exemplary figures. All features described and/or illustrated herein can be used alone or combined in different combinations. The features and advantages of various embodiments will become apparent by reading the following detailed description with reference to the attached drawings, which illustrate the following.

DETAILED DESCRIPTION

Figure 1:
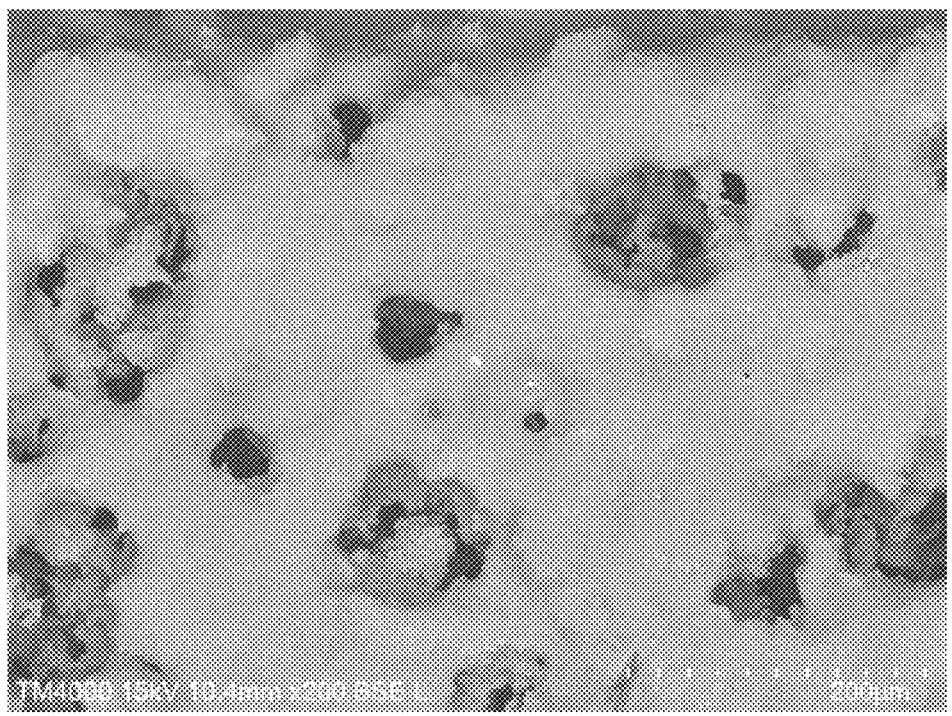
FIG. 1 is a scanning electron microscope (SEM) image at 200× magnification of a modification layer on a surface of a ceramic substrate in Example 1.

In an embodiment, the present invention provides a modification layer on a surface of a ceramic substrate. The modification layer includes the following components in parts by mass: 56 to 67.5 parts of silicon dioxide, 12 to 18 parts of aluminum oxide, and 2.8 to 5.5 parts of lithium oxide.

In an embodiment, the modification layer further includes the following components in parts by mass: at least one of 1.8 to 2.8 parts of phosphorus pentoxide, 0.5 to 2.0 parts of calcium oxide, 0.15 to 1.5 parts of magnesium oxide, and 2.5 to 5.25 parts of barium oxide.

In an embodiment, the modification layer further includes the following components in parts by mass: at least one of 0.1 to 5 parts of zirconium oxide and 0.3 to 0.45 parts of zinc oxide.

In an embodiment, the present invention provides a method for forming a modification layer on a surface of a ceramic substrate, including the following steps:

weighing raw materials according to corresponding parts by mass, and mixing and processing to obtain a mixture, wherein the raw materials comprise: 35 to 50 parts of spodumene, 1.5 to 3.5 parts of lithium carbonate, 11 to 20 parts of clay, 28 to 36 parts of silicon micropowder, and 50 to 80 parts of organic solvent, and the organic solvent comprises a viscous substance; and performing ball-milling treatment on the mixture to obtain a ball abrasive, coating the ball abrasive on a ceramic substrate, and performing sintering treatment to form the modification layer on the surface of the ceramic substrate, wherein the modification layer comprises the following components in parts by mass: 56 to 67.5 parts of silicon dioxide, 12 to 18 parts of aluminum oxide, and 2.8 to 5.5 parts of lithium oxide.

In an embodiment, the raw materials further include a flux, and the flux comprises at least one of 0.1 to 3 parts of calcium carbonate and 0.1 to 6 parts of barium carbonate.

In an embodiment, a mass percentage of the viscous substance in the organic solvent is 3% to 8%.

In an embodiment, the viscous substance is polyvinyl butyral.

In an embodiment, the organic solvent further comprises at least one of the following solvents: terpineol, oleic acid, and hydrogenated castor oil.

In an embodiment, an average particle size of the clay is 1 μm to 50 μm.

In an embodiment, an average particle size of the silicon micropowder is 1 μm to 30 μm.

In an embodiment, the organic solvent has a viscosity of 4000 cP to 10000 cP.

In an embodiment, the ball milling treatment is to perform ball milling in a ball mill at a ball milling speed of 300 r/min to 600 r/min, a ball milling time being 30 min to 120 min.

In an embodiment, the sintering treatment is to perform sintering treatment at 1100° C. to 1200° C. for 60 min to 120 min.

In an embodiment, in the step of coating the ball abrasive on a ceramic substrate, a coating manner is at least one of spray coating, brush coating, transfer printing, and screen printing.

In an embodiment, before the step of sintering treatment, the method further includes:
drying a ball abrasive coated on the ceramic substrate at 70° C. to 100° C. for 30 min to 60 min. This application further provides a ceramic heating body, including:
a ceramic substrate;
the modification layer, according to any embodiment of this application, disposed on a surface of the ceramic substrate; and
a heating layer disposed on a surface of the modification layer that is away from the ceramic substrate.

In an embodiment, a thickness of the modification layer is 50 μm to 300 μm.

This application further provides a ceramic heating body, including:
a ceramic substrate;
a modification layer formed on a surface of the ceramic substrate according to the method for forming a modification layer on a surface of a ceramic substrate according to any embodiment of this application; and
a heating layer disposed on a surface of the modification layer that is away from the ceramic substrate.

In an embodiment, a thickness of the modification layer is 50 μm to 300 μm.

This application further provides an electronic atomization device, which includes the ceramic heating body according to an embodiment of this application.

To make the foregoing objects, features and advantages of this application more comprehensible, detailed description is made to specific implementations of this application below with reference to the accompanying drawings. In the following description, many specific details are provided to facilitate a full understanding of this application. However, this application may alternatively be implemented in other manners different from those described herein, and a person skilled in the art may make similar modifications without departing from the content of this application. Therefore, this application is not limited to the embodiments disclosed below.

Unless otherwise defined, meanings of all technical and scientific terms used in this specification are the same as those usually understood by a person skilled in the art to which this application belongs. In this application, terms used in the specification of this application are merely intended to describe objectives of the specific embodiments, but are not intended to limit this application. The term "and/or" used in this specification includes any and all combinations of one or more related listed items.

A modification layer on a surface of a ceramic substrate is provided in an embodiment of this application. The modification layer includes the following components in parts by mass: 56 to 67.5 parts of silicon dioxide, 12 to 18 parts of aluminum oxide, and 2.8 to 5.5 parts of lithium oxide.

The lithium oxide can reduce an expansion coefficient of the modification layer on the surface of the ceramic substrate and improve thermal shock resistance. The obtained modification layer has a high degree of thermal match with the ceramic substrate, and is not prone to microcracks in a subsequent use process.

Further, the modification layer further includes the following components in parts by mass: at least one of 1.8 to 2.8 parts of phosphorus pentoxide, 0.5 to 2.0 parts of calcium oxide, 0.15 to 1.5 parts of magnesium oxide, and 2.5 to 5.25 parts of barium oxide.

Further, the modification layer further includes the following components in parts by mass: at least one of 0.1 to 5 parts of zirconium oxide and 0.3 to 0.45 parts of zinc oxide.

Microcracks are generated in the sintered modification layer of the conventional ceramic heating body due to two major factors. On the one hand, the modification layer is not thermally matched with the ceramic substrate in contact with the modification layer. In use, the ceramic substrate is in an environment with constant thermal cycle shocks, thus generating microcracks in the modification layer. On the other hand, the thermal shock resistance of the modification layer is poor, and microcracks are easily generated in a process of firing and cooling or thermal cycle impact. This application proposes a novel modification layer on a surface of a ceramic substrate, with components being properly matched and proportioned. That is, lithium oxide, aluminum oxide, and silicon dioxide are properly matched, and the prepared modification layer on the surface of the ceramic substrate has a high degree of thermal match with the ceramic substrate, has good thermal shock resistance, and is not prone microcracks during firing and repeated impact of thermal cycles.

This application further provides a method for forming a modification layer on a surface of a ceramic substrate, including the following steps:

S1. Weigh raw materials according to corresponding parts by mass, and mix and process to obtain a mixture, where the raw materials include: 35 to 50 parts of spodumene, 1.5 to 3.5 parts of lithium carbonate, 11 to 20 parts of clay, 28 to 36 parts of silicon micropowder, and 50 to 80 parts of organic solvent, and the organic solvent includes a viscous substance.

Lithium oxide can be generated from spodumene in a sintering reaction process, and can reduce an expansion coefficient of the modification layer on the surface of the ceramic substrate and improve thermal shock resistance. The obtained modification layer has a high degree of thermal match with the ceramic substrate, and is not prone to microcracks in a subsequent use process. In addition, using lithium-containing spodumene is better than directly adding the lithium oxide to the formula. If the lithium oxide is used instead of the spodumene, a higher sintering temperature is required, which easily causes damage to the ceramic substrate.

The lithium carbonate is mainly used to make up for the insufficient lithium content in the spodumene, and to increase the content of the lithium oxide in the modification layer. The lithium oxide is obtained after the lithium carbonate is sintered.

The clay is mainly used to generate aluminum oxide during sintering.

Further, an average particle size of the clay is 1 μm to 50 μm.

Silicon dioxide is obtained by sintering the silicon micropowder.

Specifically, an average particle size of the silicon micropowder is 1 μm to 30 μm.

The organic solvent containing the viscous substance is mainly used to dissolve other components on the surface of the modification layer of the ceramic substrate and bond the components together after drying to form the modification layer on the surface of the ceramic substrate. Further, the viscous substance is polyvinyl butyral.

Specifically, a mass percentage of the viscous substance in the organic solvent is 3% to 8%.

Specifically, the organic solvent has a viscosity of 4000 cP to 10000 cP, so that the components of the modification layer are bonded together and are not prone to precipitation. If the organic solvent is replaced with water, after the lithium carbonate is dissolved in water, the components of the mixture will be unevenly distributed. Further, the organic solvent further includes terpineol. Further, the organic solvent further includes at least one of oleic acid and hydrogenated castor oil. By using the oleic acid as a leveling agent and the hydrogenated castor oil as a thixotropic agent, the leveling performance of the organic solvent can be improved.

Further, the raw materials of the modification layer further include a flux that includes at least one of 0.1 to 3 parts of calcium carbonate and 0.1 to 6 parts of barium carbonate. In a subsequent raw material sintering process, the flux helps to reduce a sintering temperature, promote the melting and reaction of the raw materials, and form a surface modification layer with good thermal shock resistance and no microcracks. The calcium carbonate becomes the calcium oxide after sintering, and the barium oxide becomes the barium oxide after sintering.

Further, the modification layer further includes at least one of 0.1 to 2 parts of zirconium oxide and 0.1 to 3 parts of zinc oxide. The zirconium oxide and the zinc oxide act as crystallization agents to promote formation of crystal nuclei.

S2. Perform ball-milling treatment on the mixture to obtain a ball abrasive, coat the ball abrasive on a ceramic substrate, and perform sintering treatment to form a modification layer on a surface of the ceramic substrate. It is measured through experiments that the obtained modification layer includes the following components in parts by mass: 56 to 67.5 parts of silicon dioxide, 12 to 18 parts of aluminum oxide, and 2.8 to 5.5 parts of lithium oxide.

Optionally, the ball milling treatment is to perform ball milling treatment in a ball mill, and a specific process is as follows: a ball milling speed is 300 r/min to 600 r/min, and a ball milling time is 30 min to 120 min.

Optionally, in a step of coating the ball abrasive on a ceramic substrate, a coating manner may be selected from various coating manners such as spray coating, brush coating, transfer printing and screen printing, or the like, which are not limited herein. Further, the transfer printing is used for coating.

Specifically, the sintering treatment is to perform sintering treatment at 1100° C. to 1200° C. for 60 min to 120 min.

Further, before the step of sintering treatment, a preparation method of the modification layer further includes drying the ball abrasive coated on the ceramic substrate at 70° C. to 100° C. for 30 min to 60 min.

The preparation method for the modification layer on the surface of the ceramic substrate is simple, and the modification layer with good thermal matching with the ceramic substrate may be obtained at a relatively low sintering temperature.

The performance of the ceramic heating body is generally affected by the quality of the ceramic substrate. Therefore, the surface of the ceramic substrate needs to be modified to form a continuous porous grid structure on the surface of the ceramic substrate, so as to facilitate the uniform heating and liquid conduction of the ceramic heating body. Although glass frit or alkaline metal oxides (such as sodium silicate, potassium sodium tartrate, borax) may be used as a modification layer to form a continuous porous grid structure on the surface of the ceramic substrate, after such a modification layer is fired and formed, problems of poor thermal shock resistance and microcracks may occur, and even a heating layer of the ceramic heating body may break during use.

Microcracks are generated in the sintered modification layer of the conventional porous ceramic heating body due to two major factors. On the one hand, the modification layer is thermally matched with the ceramic substrate in contact with the modification layer. During use, the ceramic substrate is in an environment of constant thermal cycle shocks, and the microcracks are generated in the modification layer. On the other hand, the thermal shock resistance of the modification layer is poor, and microcracks are easily generated in a process of firing and cooling or thermal cycle impact. In this application, high-temperature molten materials with low expansion coefficients, such as spodumene and silica, are used, and are properly matched with clay, lithium carbonate and organic solvent in proportion to each other. The prepared modification layer on the surface of the ceramic substrate has a high degree of thermal matching with the ceramic substrate, has good thermal shock resistance, and is not prone to microcracks during firing and repeated impact of thermal cycles.

Figure 6:
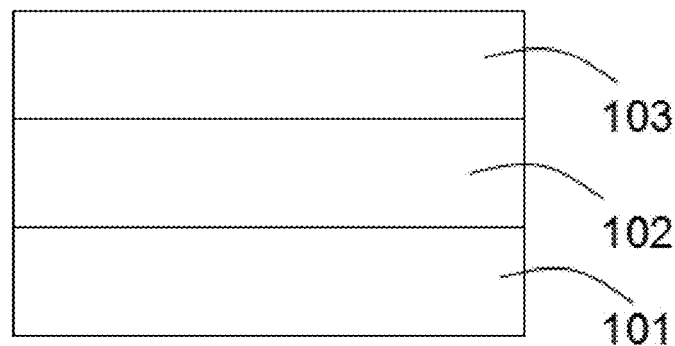
FIG. 6 is a front view of a structure of a ceramic heating body according to an embodiment of this application.

Referring to FIG. 6, this application further provides a novel ceramic heating body, which includes: a ceramic substrate 101, and a modification layer 102, according to any one of the embodiments, disposed on a surface of the ceramic substrate 101; and a heating layer 103 disposed on a surface of the modification layer 102 that is away from the ceramic substrate 101.

This application further provides a novel ceramic heating body, which includes: a ceramic substrate 101, a modification layer 102 formed on a surface of the ceramic substrate 101 according to the method for forming the modification layer 102 on a surface of a ceramic substrate according to any one of the embodiments, and a heating layer 103 disposed on a surface of the modification layer 102 that is away from the ceramic substrate 101.

Optionally, the ceramic substrate 101 is a porous ceramic substrate, such as diatomite porous ceramics, aluminum oxide porous ceramics, mullite porous ceramics, and composite porous ceramics including at least two of the foregoing materials, for example, composite porous ceramics including aluminum oxide and mullite.

Specifically, a thickness of the modification layer 120 is 50 μm to 300 μm.

Optionally, the heating layer 103 is a thin film heating layer. Specifically, the heating layer 103 is a printed circuit. More specifically, the printed circuit is made by the following processing manner: a metal paste is screen-printed on one surface of the modification layer 102 on the surface of the ceramic substrate 101 according to any one of the embodiments, and is then sintered. In this case, the modification layer 102 and the heating layer 103 are integrally formed to obtain a ceramic heating body.

Optionally, the metal paste is at least one of a platinum paste, a tungsten paste, and a titanium paste.

Specifically, the metal paste includes metal particles. Further, a particle size of a metal particle $D_{50}$ is 0.35 μm to 0.65 μm.

The modification layer 102 in the novel ceramic heating body has good thermal matching with the ceramic substrate 101, has good thermal shock resistance under the impact of thermal cycles, and is not prone to internal microcracks.

This application further provides an electronic atomization device, which includes the ceramic heating body according to an embodiment of this application. Specifically, the electronic atomization device may be an electronic cigarette.

This application further provides an application of the ceramic heating body according to this application in an electronic atomization device.

The ceramic heating body of this application may be used as an atomizing core of an electronic atomization device, and is not prone to damage after being subjected to impact of a plurality of thermal cycles, thereby prolonging the service life of the atomizing core. A person skilled in the art may understand that the ceramic heating body may be mounted in the electronic atomization device by using conventional technical means.

To make the objectives and advantages of this application clearer and more understandable, this application is further described in detail below with reference to the embodiments. It is to be understood that the specific embodiments described herein are merely used for explaining this application, but are not intended to limit this application.

Example 1

A preparation process of a modification layer on a surface of a ceramic substrate is as follows:

Australian spodumene ($D_{50=3 \ \mu m \ to \ 5 \ \mu m}$) was taken. Silicon micropowder was passed through a 5000-mesh sieve; lithium carbonate, calcium carbonate and barium carbonate were passed through a 325-mesh sieve. Suzhou clay calcined at 1000° C. and passed through a 320-mesh sieve was used. A specific formula is shown in Table 1 below.

TABLE 1

| Australian spodumene | Silicon micro- powder | Clay (calcined) | Lithium carbonate | Barium carbonate | Calcium carbonate |
|---|---|---|---|---|---|
| 47.8 parts | 30 parts | 11 parts | 2.4 parts | 5.8 parts | 3 parts |

Components in Table 1 were mixed, then added to 70 parts of terpineol (including 4% of polyvinyl butyral (PVB)). Ball milling treatment was performed at 500 r/min for 60 min, followed by transfer printing. The transfer printing process was performed in the following manner: A film of a certain thickness was prepared from the prepared materials on a piece of tallow paper by using a film scraper; then the tallow paper was transferred to a soft silicone sheet and fixed well; the fixed diatomite porous ceramic was inverted on a piece of kraft paper with a coating material; after uniform pressure was applied and standing for 10 s, the porous ceramic substrate was quickly lifted; then the excess paste on the surface and sides of the porous ceramic was brushed off with a soft wool brush, and the substrate was placed in a drying oven at 80° C. for 30 min. The foregoing transfer printing process was repeated and the substrate was sintered at 1150° C. for 60 min, to form a modification layer with a thickness of 200 μm on the surface of the porous ceramic. Upon measurement, mass percentages of the components in the modification layer were as follows: 3.69% of lithium oxide, 16.64% of aluminum oxide, 66.42% of silicon dioxide, 4.48% of barium oxide, 2.12% of calcium oxide, 2.1% of phosphorus pentoxide, 0.54% of potassium oxide, 0.41% of sodium oxide, 0.15% of magnesium oxide, and 0.51% of iron oxide.

Example 2

A preparation process of a modification layer on a surface of a ceramic substrate is as follows, and the steps are generally the same as those in Example 1, except that the modification layer on the surface of the ceramic substrate has a different formula. Refer to Table 2 for details.

TABLE 2

| Australian spodumene | Silicon micro- powder | Clay (calcined) | Lithium carbonate | Calcium carbonate | Zinc oxide |
|---|---|---|---|---|---|
| 47.5 parts | 33 parts | 11.5 parts | 2.5 parts | 3 parts | 2.5 parts |

Example 3

A preparation process of a modification layer on a surface of a ceramic substrate is as follows, and the steps are generally the same as those in Example 1, except that a ceramic substrate is aluminum oxide porous ceramics, and the modification layer on the surface of the ceramic substrate has a different formula. Refer to Table 3 for details.

TABLE 3

| Australian spodu- mene | Silicon micro- powder | Clay (cal- cined) | Lithium carbon- ate | Barium carbon- ate | Zirco- nium oxide | Zinc oxide |
|---|---|---|---|---|---|---|
| 43 parts | 29 parts | 18 parts | 2 parts | 3.5 parts | 1.5 parts | 3 parts |

Comparative Example 1

A preparation process of a modification layer on a surface of a ceramic substrate is as follows. 30 parts of glass powder were taken and added to terpineol (including 4% of PVB), and a ball milling treatment was performed at 500 r/min for 60 min to obtain a prepared paste for transfer printing. The transfer printing process was as follows. A film of a certain thickness was prepared from the prepared materials on a piece of tallow paper by using a film scraper; then the tallow paper was transferred to a soft silicone sheet and fixed well; the fixed diatomite porous ceramic was inverted on a piece of kraft paper with a coating material; after uniform pressure was applied and standing for 10 s, the porous ceramic substrate was quickly lifted; then the excess paste on the surface and sides of the porous ceramic was brushed off with a soft wool brush, and the substrate was placed in a drying oven at 80° C. for 30 min. The foregoing transfer printing process was repeated and the substrate was sintered at 900° C. for 60 min to form a modification layer with a thickness of 200 μm on the surface of the porous ceramic.

Comparative Example 2

A preparation process of a modification layer on a surface of a ceramic substrate is as follows: Solid sodium silicate was grinded, 30 parts of the grinded solid sodium silicate with a particle size of 10 μm were taken and added to terpineol (including 4% of PVB), and a ball milling treatment was performed at 500 r/min for 60 min to obtain a prepared paste for transfer printing. The transfer printing process was as follows. A film of a certain thickness was prepared from the prepared materials on a piece of tallow paper by using a film scraper; then the tallow paper was transferred to a soft silicone sheet and fixed well; the fixed diatomite porous ceramic was inverted on a piece of kraft paper with a coating material; after uniform pressure was applied and standing for 10 s, the porous ceramic substrate was quickly lifted; then the excess paste on the surface and sides of the porous ceramic was brushed off with a soft wool brush, and the substrate was placed in a drying oven at 80° C. for 30 min. The foregoing transfer printing process was repeated and the substrate was sintered at 1050° C. for 60 min to form a modification layer with a thickness of 200 μm on the surface of the porous ceramic.

Thermal Shock Performance Test

Figure 2:
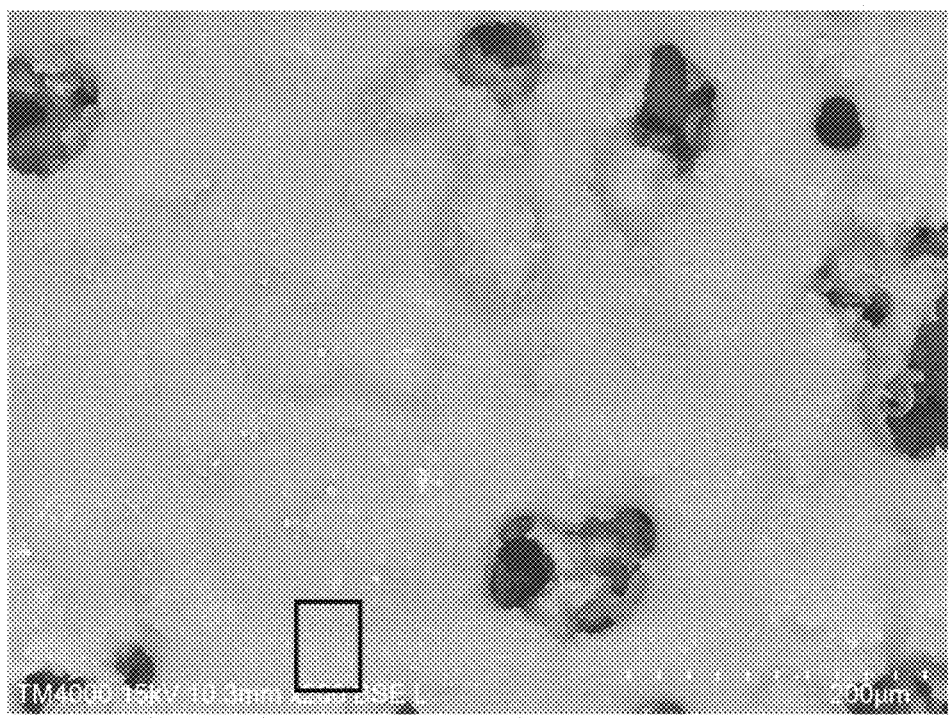
FIG. 2 is a SEM image at 200× magnification of a modification layer on a surface of a ceramic substrate in Example 2.

Samples of Example 1 and Example 2 were heated to 600° C. and the temperature was kept for 20 min; then the samples were quickly put into 30° C. water for quenching to obtain SEM images at 200× magnification. Refer to FIG. 1 and FIG. 2 for details.

Figure 4:
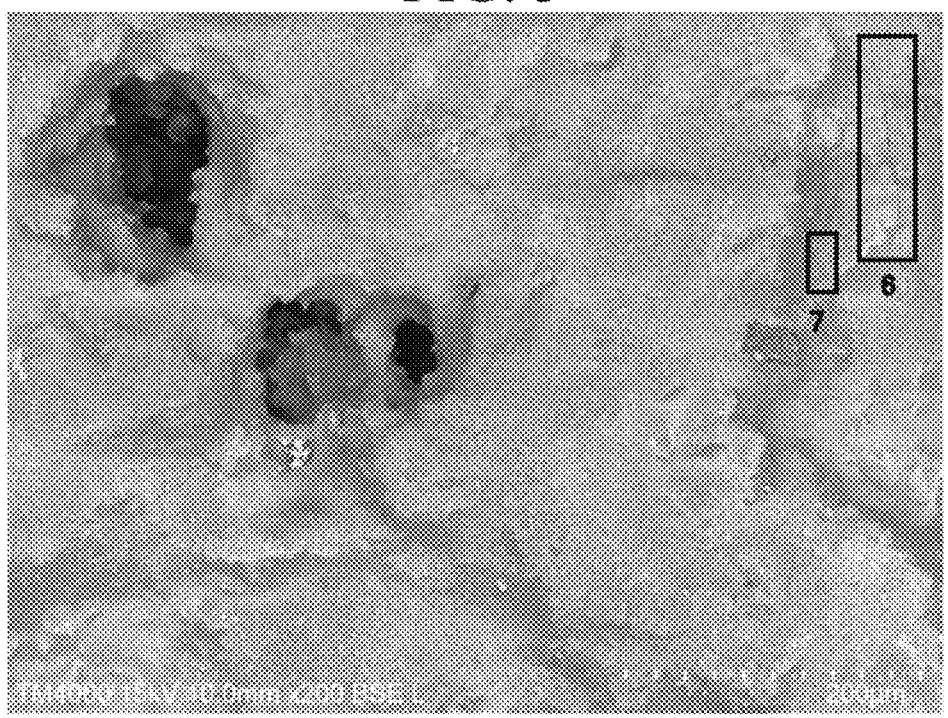
FIG. 4 is a SEM image at 200× magnification of a modification layer on a surface of a ceramic substrate in Comparative Example 1.
Figure 5:
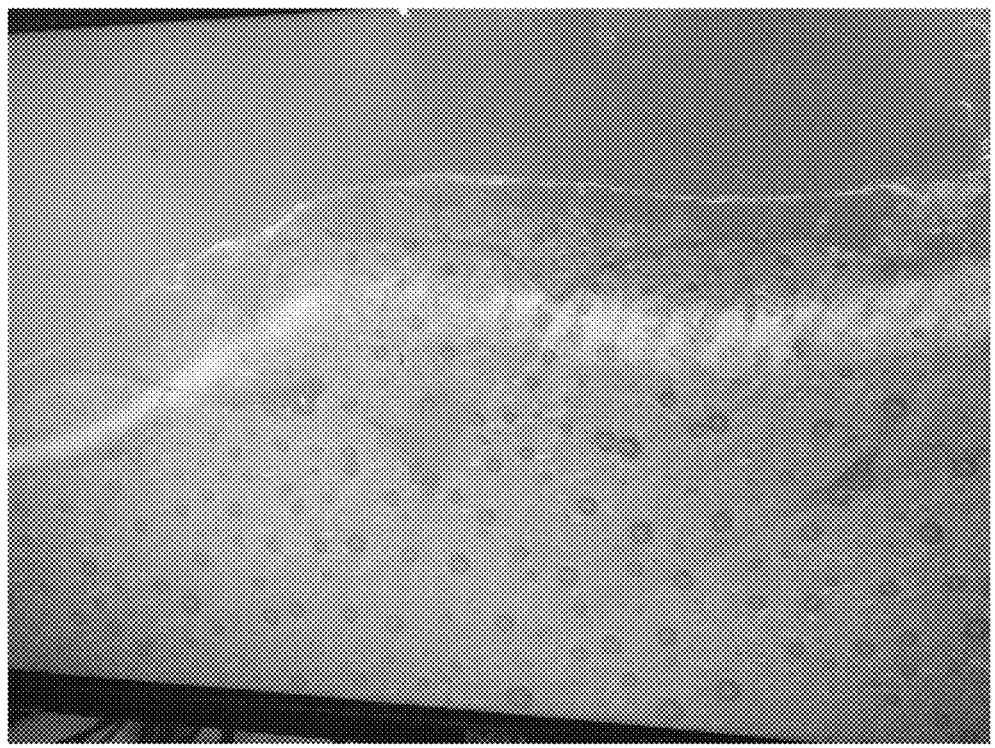
FIG. 5 is a picture of a modification layer on a surface of a physical ceramic substrate in Comparative Example 2.

Samples of Comparative Example 1 and Comparative Example 2 were heated to 1000° C. and melted to form a transparent glaze layer, obvious cracks on the surface of the modification layer were observed with naked eyes. Refer to FIG. 4 and FIG. 5 for details.

Test Results

Figure 3:
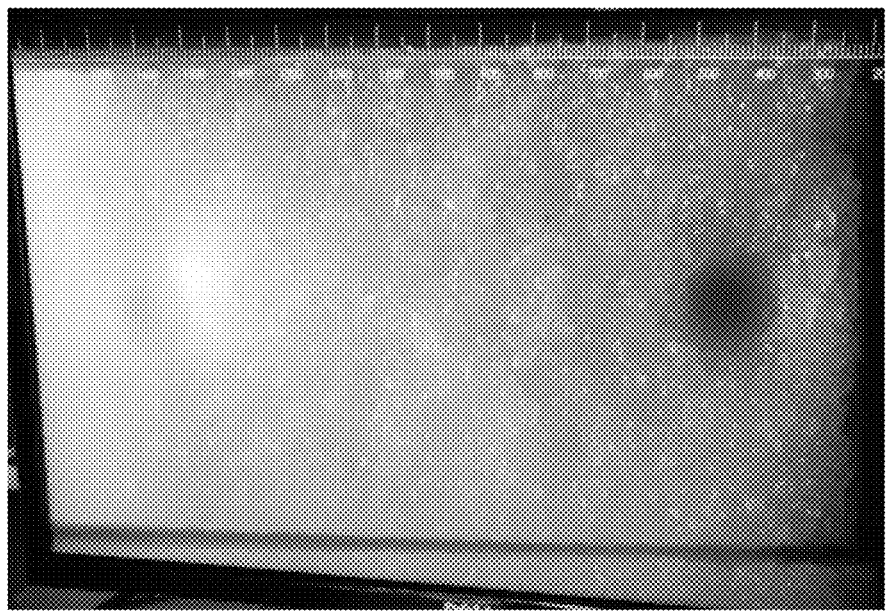
FIG. 3 is a picture of a surface of a modification layer on a surface of a ceramic substrate in Example 1.

It can be seen from FIG. 1 (Example 1) and FIG. 2 (Example 2) under an electron microscope at 200× magnification that few and very short cracks are generated in the modification layer on the surface of the ceramic substrate. In FIG. 3, cracks in the modification layer on the surface of the ceramic substrate of Example 1 are hardly visible to naked eyes. In FIG. 4 (Comparative Example 1), obvious cracks can be seen in a frame 7 under an electron microscope at 200× magnification. Clear cracks are also visible to naked eyes in FIG. 5 (Comparative Example 2). It shows that the modification layer on the surface of the ceramic substrate of this application has good thermal shock resistance and is not prone to cracks.

The technical features in the above embodiments may be randomly combined. For concise description, not all possible combinations of the technical features in the embodiment are described. However, provided that combinations of the technical features do not conflict with each other, the combinations of the technical features are considered as falling within the scope recorded in this specification.

The foregoing embodiments merely express several implementations of this application. The descriptions thereof are relatively specific and detailed, but should not be understood as limitations to the scope of this application. For a person of ordinary skill in the art, several transformations and improvements can be made without departing from the idea of this application. These transformations and improvements belong to the protection scope of this application. Therefore, the protection scope of the patent of this application shall be subject to the appended claims.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

What is claimed is:

1. A method for forming a modification layer on a surface of a ceramic substrate, comprising:
    weighing raw materials of corresponding parts by mass;
    mixing and processing the raw materials to obtain a mixture, the raw materials comprising: 35 to 50 parts of spodumene, 1.5 to 3.5 parts of lithium carbonate, 11 to 20 parts of clay, 28 to 36 parts of silicon micropowder, and 50 to 80 parts of organic solvent, and the organic solvent comprising a viscous substance;
    performing ball-milling treatment on the mixture to obtain a ball abrasive;
    coating the ball abrasive on a ceramic substrate; and
    performing sintering treatment to form the modification layer on the surface of the ceramic substrate,
    wherein the modification layer comprises, in parts by mass: 56 to 67.5 parts of silicon dioxide, 12 to 18 parts of aluminum oxide, and 2.8 to 5.5 parts of lithium oxide.

2. The method of claim 1, wherein the raw materials further comprise a flux, the flux comprising at least one of 0.1 to 3 parts of calcium carbonate and 0.1 to 6 parts of barium carbonate.

3. The method of claim 1, wherein a mass percentage of the viscous substance in the organic solvent is 3% to 8%.

4. The method of claim 1, wherein the viscous substance comprises polyvinyl butyral.

5. The method of claim 1, wherein the organic solvent further comprises at least one of the following solvents: terpineol, oleic acid, and hydrogenated castor oil.

6. The method of claim 1, wherein an average particle size of the clay is 1 μm to 50 μm.

7. The method of claim 1, wherein an average particle size of the silicon micropowder is 1 μm to 30 μm.

8. The method of claim 1, wherein the organic solvent has a viscosity of 4000 cP to 10000 cP.

9. The method of claim 1, wherein the ball-milling treatment comprises ball milling in a ball mill at a ball milling speed of 300 r/min to 600 r/min, a ball milling time being 30 min to 120 min.

10. The method of claim 1, wherein the sintering treatment comprises sintering at 1100° C. to 1200° C. for 60 min to 120 min.

11. The method of claim 1, wherein coating the ball abrasive on the ceramic substrate comprises at least one of spray coating, brush coating, transfer printing, and screen printing as a coating manner.

12. The method of claim 1, wherein before performing sintering treatment, the method further comprises:
    drying a ball abrasive coated on the ceramic substrate at 70° C. to 100° C. for 30 min to 60 min.

13. A ceramic heating body, comprising:
    a ceramic substrate;

a modification layer formed on a surface of the ceramic substrate according to the method of claim 1; and a heating layer disposed on a surface of the modification layer that is away from the ceramic substrate.

14. The ceramic heating body of claim 13, wherein a thickness of the modification layer is 50 μm to 300 μm.

* * * * *